Figure 1:
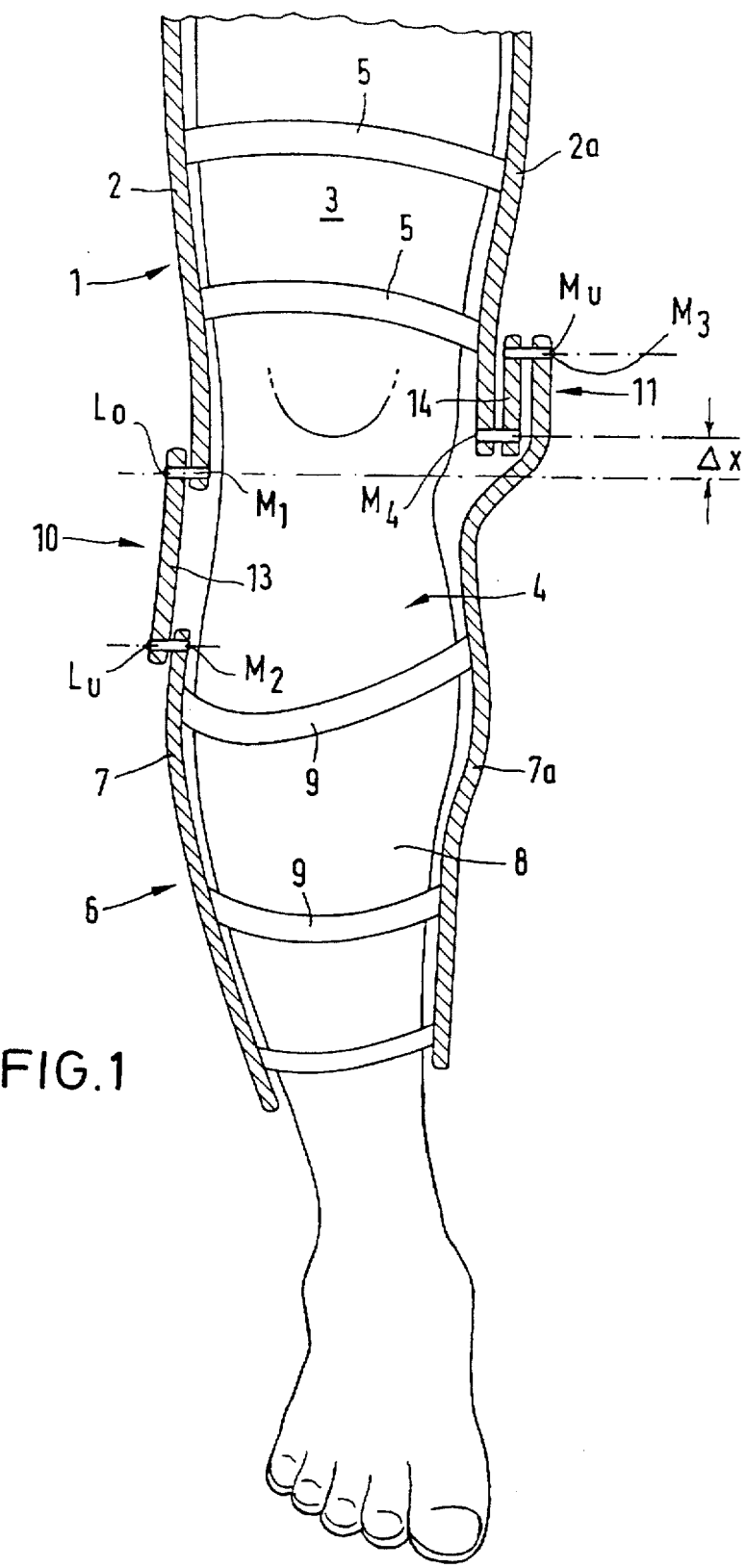

United States Patent [19]

Kubein-Meesenburg et al.

[11] Patent Number: 5,800,370
[45] Date of Patent: Sep. 1, 1998

[54] EXOPROSTHESIS FOR THE HUMAN KNEE JOINT

[75] Inventors: Dietmar Kubein-Meesenburg, Kreiensen; Hans Nagerl, Klein-Lengden, both of Germany

[73] Assignee: Joachim Theusner, Munich, Germany

[21] Appl. No.: 525,718

[22] PCT Filed: Feb. 16, 1994

[86] PCT No.: PCT/EP94/00433

§ 371 Date: Dec. 22, 1995

§ 102(e) Date: Dec. 22, 1995

[87] PCT Pub. No.: WO94/21200

PCT Pub. Date: Sep. 29, 1994

[30] Foreign Application Priority Data

Mar. 24, 1993 [DE] Germany ............ 43 09 577.1

[51] Int. Cl.$^6$ .................. A61F 5/00; A61F 2/64
[52] U.S. Cl. .................. 602/26; 602/16; 602/23; 623/39
[58] Field of Search .................. 602/5, 16, 23, 602/26; 623/27, 28, 39, 32

[56] References Cited

U.S. PATENT DOCUMENTS

| | | | |
|---|---|---|---|
| 2,570,382 | 10/1951 | Ruetting | 602/16 |
| 3,581,741 | 6/1971 | Rasman | 602/16 X |
| 3,885,252 | 5/1975 | Nakajima | 602/26 |
| 3,901,223 | 8/1975 | May | 602/26 |
| 4,064,874 | 12/1977 | Valin | 602/26 |
| 4,241,730 | 12/1980 | Helfet | 602/26 |
| 4,271,831 | 6/1981 | Deibert | 602/16 |
| 4,395,783 | 8/1983 | Eyre et al. | 623/27 X |
| 4,603,690 | 8/1986 | Skeen | 602/16 |
| 4,854,308 | 8/1989 | Drillio | 602/16 |
| 4,911,709 | 3/1990 | Marlow et al. | 623/39 |
| 4,966,133 | 10/1990 | Kausek | 602/26 X |
| 5,013,037 | 5/1991 | Stermer | 602/26 X |
| 5,201,776 | 4/1993 | Freeman | 602/26 |
| 5,458,565 | 10/1995 | Tillinghast, III | 602/26 |

Primary Examiner—Richard J. Apley
Assistant Examiner—Denise Pothier
Attorney, Agent, or Firm—Jones & Askew, LLP

[57] ABSTRACT

The present invention relates to an exoprosthesis for the human knee joint consisting of a thigh part (1) which can be connected to the human thigh as well as a lower leg part (6) which can be connected to the human lower leg or which can replace it. The lower leg part (6) and the thigh part (1) are connected through a four-bar arrangement which consists of two parallel arranged partial joints, specifically a medial joint (11) and a lateral joint (10) each of which has the joint geometry of a link chain with two articulated axles ($M_u$, $M_o$; $L_o$, $L_u$) (dimer link chains). The joint geometry of the medial joint (11) is designed as an overlapping, dimer link chain in which the articulated axle $M_u$ of the lower leg part (6) is displaced in the direction towards the thigh part (1) with respect to the articulated axle $M_o$ of the thigh part (1) and the joint geometry of the lateral joint (10) is designed as an extended dimer chain in which the articulated axle $L_u$ of the lower leg part (6) is displaced with respect to the articulated axle $L_o$ of the thigh part (1) in the direction towards the lower leg (8). Both articulated axles of the lateral joint (10) and the medial joint (11) are connected with one another in an articulated manner in each case by means of a coupling link (13,14).

4 Claims, 6 Drawing Sheets

EXOPROSTHESIS FOR THE HUMAN KNEE JOINT

The present invention relates to an exoprosthesis for the human knee joint.

The known exoprostheses for the human knee joint are multiple-joint arrangements using ball joints and/or hinge joints. Such joint arrangements, however, are not suitable for approximating the actual function of the human knee joint in an essentially natural manner, so that these exoprostheses cause a considerable walking impediment.

The object of the invention is to create an exoprosthesis for the human knee joint which has a joint function which essentially corresponds to the natural function of the human knee joint.

According to the invention this is achieved in that the exoprosthesis consists of a thigh part which can be connected to the human thigh as well as a lower leg part which can be connected to the human lower leg or can replace it, whereby the lower leg part and the upper leg part are connected by a four-bar arrangement which consists of two parallel arranged partial joints and, specifically, a medial joint and a lateral joint which in each case have the joint geometry of a link chain with two articulated axles (dimer joint chains), whereby the joint geometry of the medial joint is designed as an overlapping, dimer link chain in which the articulated axle of the lower leg part is displaced in the direction towards the thigh part with respect to the articulated axles of the thigh part, and the joint geometry of the lateral joint is designed as an extended dimer chain in which the articulated axle of the lower leg part is displaced with respect to the articulated axis of the thigh part in the direction towards the lower leg and the two articulated axles of the lateral joint and the medial joint each are connected in an articulated manner to one another by means of a coupling link. The medial joint is stable with regard to pressure due to its joint geometry, whereas the lateral joint is labile. By means of the design according to the invention, it is assured that the exoprosthesis has freedom of movement in only one joint plane and at the same time high mechanical stability is achieved whereby a great spectrum of variation is available for adaptation to individual situations.

Figure 2:
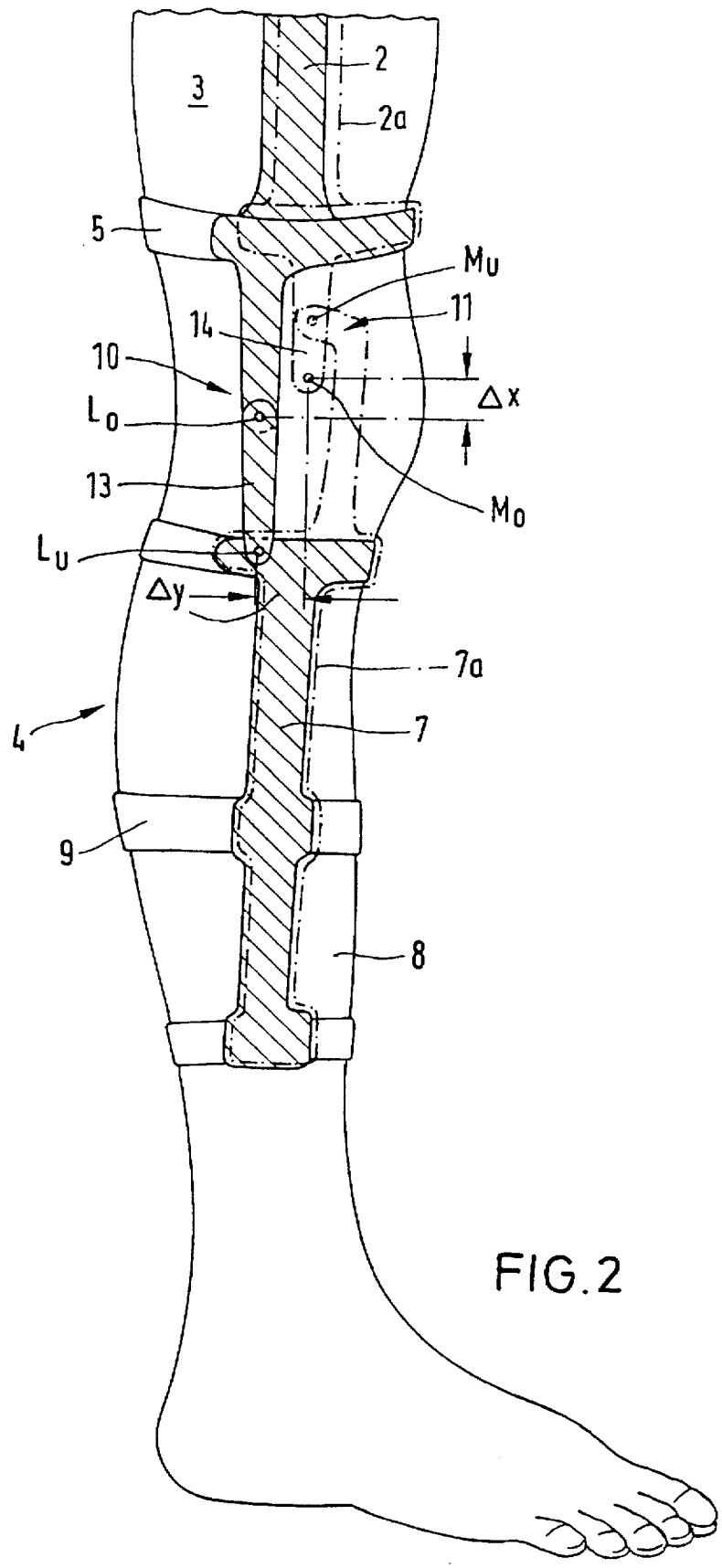
Figure 3:
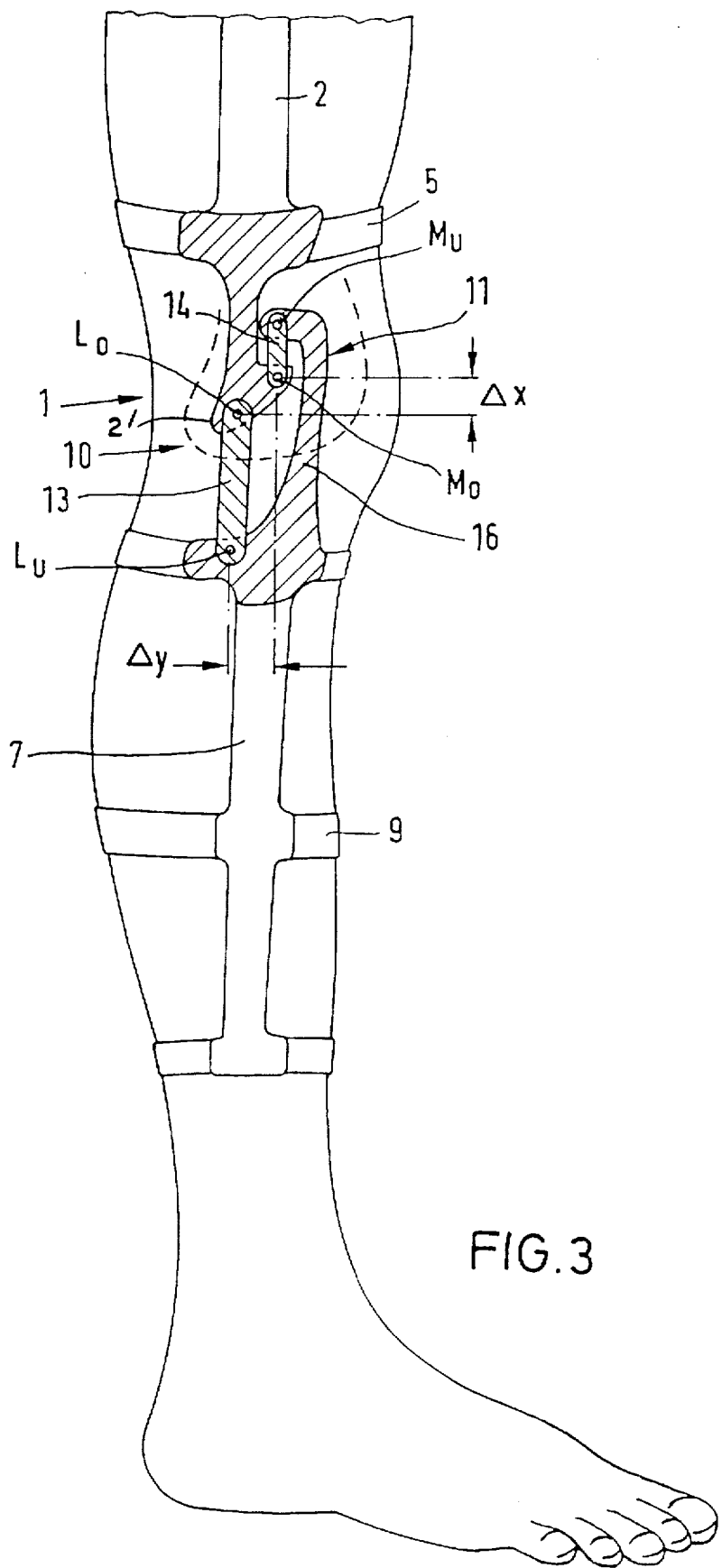
Figure 4:
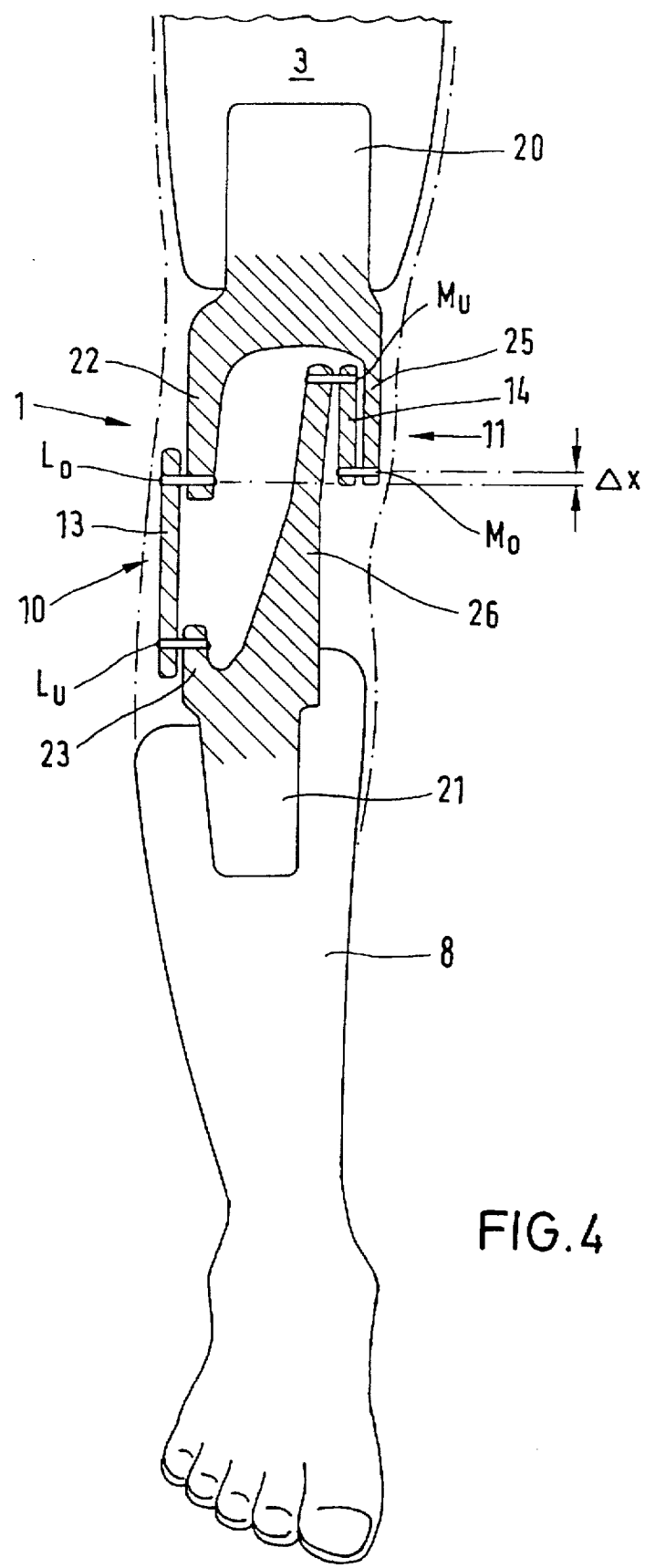
Figure 5:
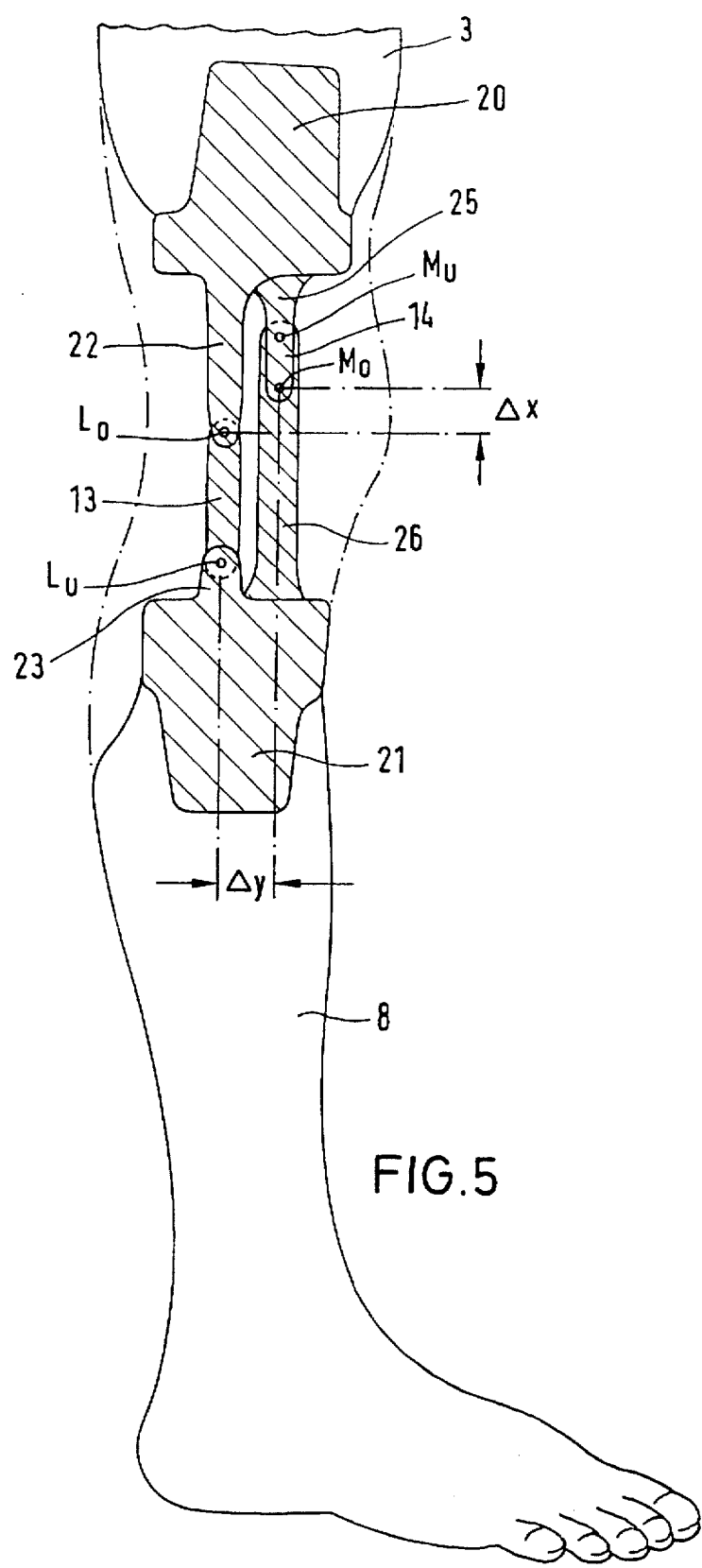

The invention is explained in more detail on the basis of the embodiment examples presented in the attached drawings. Shown are:

FIG. 1, a frontal view of an exoprosthesis according to the invention in the state fastened to a human leg, cut in section, FIG. 2, a side view according to arrow II in FIG. 1, FIG. 3, a side view of another embodiment form of a prosthesis according to the invention in the state fastened to the human leg, FIG. 4, a cut through another embodiment form of an exoprosthesis according to the invention as a replacement of the human knee joint, FIG. 5, a side view of the exoprosthesis according to the invention according to FIG. 4 in the direction of arrow V.

Figure 6:
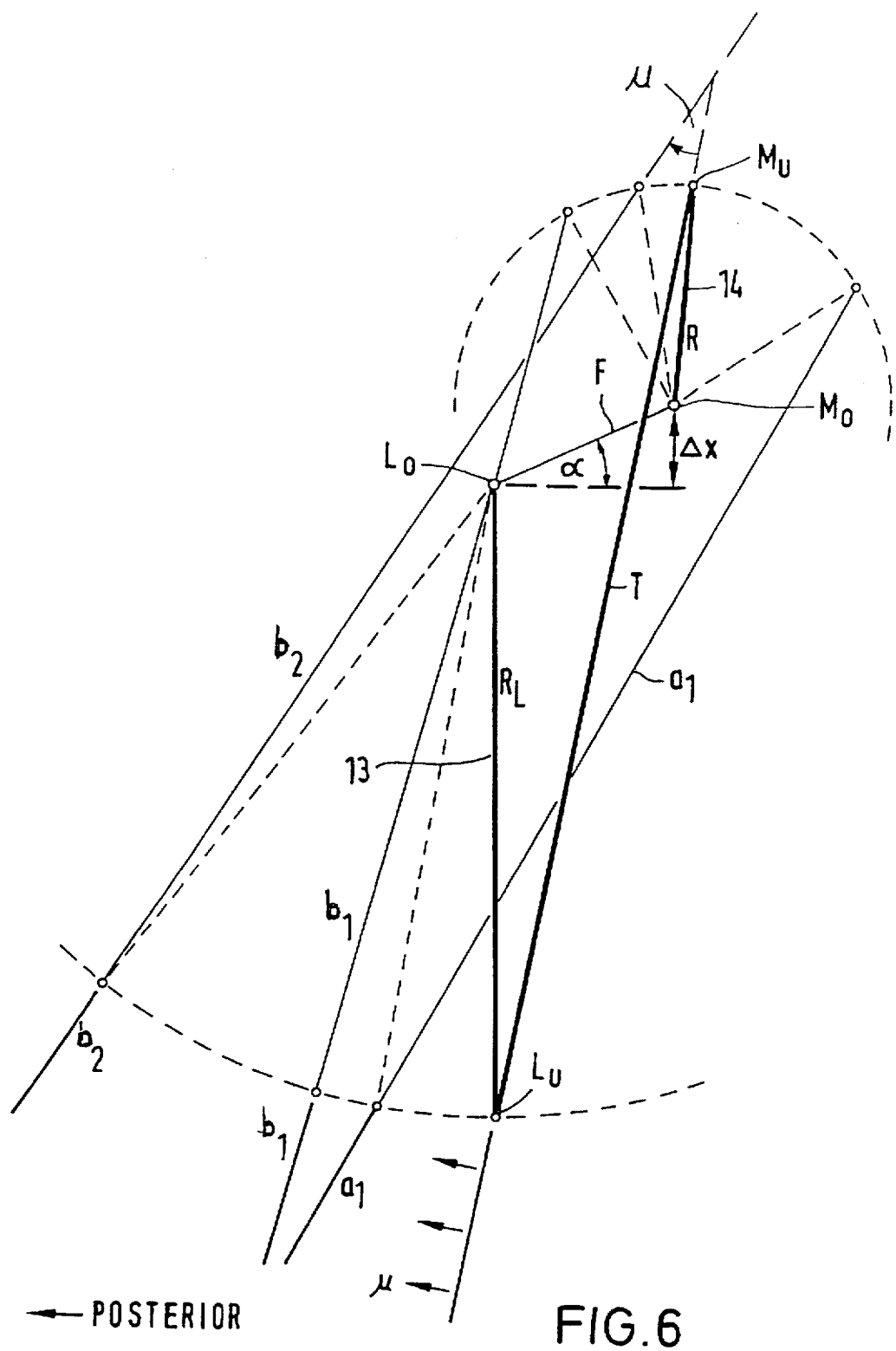

FIG. 6, a presentation in principle of the joint geometry in the side view according to FIG. 2.

As shown in FIG. 1, a prosthesis according to the invention consists of thigh part 1, which consists, in the presented embodiment example, of two thigh bars 2,2a which in each case run on the medial (inner) and lateral (outer) side of thigh 3 of human leg 4 and are connected to one another through cross bars 5 which encircle thigh 3. Lower leg part 6 is formed from two lower leg bars 7,7a on the medial and lateral side of lower leg 8 of leg 4 which are connected by cross bars 9 whereby cross bars 9 in turn surround lower leg 8. Lateral thigh and lower leg bars 2,7 as well as medial thigh and lower leg bars 2a, 7a are connected in each case through a double joint, specifically lateral joint 10 and medial joint 11, which lie adjacent to one another in two parallel planes, that is, the two parallel arranged double joints form a four-bar arrangement. Lateral joint 10 and medial joint 11 have the joint geometry of a link chain with two articulated axles, a so-called dimer link chain. Here, lateral joint 10 is designed as an extended, dimer link chain with the two articulated axles $L_o$, $L_u$, whereby articulated axle $L_o$ is connected to articulated axle $L_u$ by coupling link 13, in an articulated manner. Articulated axles $L_o$ and $L_u$ have the rotation centers $M_1$ and $M_2$, and run perpendicular to the sagittal plane or perpendicular to the pivotal plane of leg 6. In the extended leg position represented, articulated axles $L_o$ and $L_u$ are at an interval from one another, specifically, $L_o$ displaced in the direction towards thigh 3 and articulated axle $L_u$ displaced in the direction towards the lower leg. Coupling links 13 and 14 are arranged parallel and vertically in the standing position.

Medial joint 11 is designed as an overlapping, dimer link chain, whereby articulated axle $M_u$ of lower leg bar 7a is displaced in the direction towards thigh 3 with respect to articulated axle $M_o$ of thigh bar 2a, and specifically with reference to the extended leg position represented. Both articulated axles $M_u$ and $M_o$ are connected to one another in an articulated manner by coupling link 14. The construction of this arrangement is functionally realized in that both bars 2a and 7a overlap on their ends, and in the area of overlap, coupling link 14 is mounted between bars 2a and 7a, and is connected in an articulated manner at one end to articulated axle $M_u$ and at the other end to articulated axle $M_o$. So that the overlapping or folded, arrangement is possible, lower leg bar 7a is bent in the medial direction or thigh bar 2a is bent in the lateral direction. Furthermore, it is to be recognized that articulated axle $M_o$ of thigh bar 2a of medial joint 11 is functionally displaced with respect to articulated axle $L_o$ of thigh bar 2 of lateral joint 10 by the displacement measure Δx in the direction towards the thigh part. Furthermore, in the side view according to FIG. 2, it can be seen that articulated axle $L_o$ is functionally displaced with respect to articulated axle $M_o$ in the posterior direction by the displacement amount Δy. In the extended dimer chain of lateral joint 10, the rotation center $M_2$ in $L_u$ moves relative to the rotation center $M_1$ in $L_o$ or in the other direction on a circular path around $M_1$ with a radius R which corresponds to the interval of axles $L_o$ and $L_u$. Here, R is the relevant length of coupling length 13. In the overlapping dimer chain of medial joint 11, rotation center $M_3$ in $M_u$ moves relative to rotation center $M_4$ in $M_o$ or in the other direction on a circular path around rotation center $M_3$ with the radius RL, which corresponds to the interval of axles $M_u$ and $M_o$ which in turn represents the relative length of coupling link 14. Regarding the above movements along a circular path, rotations occur around each of the rotation centers $M_1$ to $M_4$.

Whereas FIGS. 1 and 2 show how the exoprosthesis according to the invention is designed to grip the human diseased knee bilaterally, FIG. 3 shows an embodiment form in which the four-bar arrangement according to the invention is fastened unilaterally to the human diseased knee, for example, laterally. In this case, the same parts as in FIGS. 1 and 2 are provided with the same reference numbers. The design of lateral joint 10 corresponds to the design according to FIGS. 1 and 2. Medial joint 11 is constructed from extension 16 on lower leg bar 7 which overlaps the bearing end of thigh bar 2 and, seen laterally in the direction towards the human knee, ends behind the bearing end 2 of thigh bar 2 so that lateral joint 10 and medial joint 11 are arranged parallel to one another whereby coupling link 14 of medial joint 11, also seen in the direction towards the knee is hinged behind thigh bar 2 through articulated axle M to its bearing tip.

In FIGS. 4 and 5, an embodiment form of an exoprosthesis is represented in which the human knee joint is completely and permanently replaced by the latter, whereas the embodiments according to FIGS. 1 to 3 are intended only as aids, when the existing human knee is not itself capable of performing the normal joint function. In FIGS. 4 and 5, in turn, the same parts as in FIGS. 1 and 3 are provided with the same reference numbers. Lateral joint 10 and medial joint 11 are in this case fastened to thigh stump 20 which can be implanted and lower leg stump 21 which may be part of a lower leg prosthesis. Lateral joint 10 is constructed from bearing extension 22 designed on thigh stump 20 and bearing extension 23 designed on lower leg stump 21 which are connected in an articulated manner through coupling link 13, for which coupling link 13 is fastened in an articulated manner through articulated axle $L_o$ to bearing extension 22 and through articulated axle $L_u$ to bearing extension 23. Medial joint 11 is constructed from joint extension 25 on thigh stump 20 and joint extension 26 on lower leg stump 21, whereby joint extension 26 overlaps joint extension 25 and lies between joint extension 25 and bearing extension 22. Coupling link 14 is arranged spatially between the two joint extensions 25,26 and is connected in an articulated manner with the free end of joint extension 26 through joint axle $M_u$ and with the free end of joint extension 25 through articulated axle $M_o$. As evident from the representation here, a displacement of lateral joint 10 towards the posterior with respect to medial joint 11 by the amount $\Delta y$ is advantageously provided, and articulated axle $M_o$ is displaced with respect to articulated axle $L_o$ by the displacement amount $\Delta x$ in the direction of the thigh.

Furthermore, it is within the scope of the invention that coupling links 13,14 are fastened interchangeably so that using the other prosthesis parts, the joint geometry can be changed by a change of the length of coupling links 13,14, and can be adapted to the specific situations in each case. It can also be provided according to the invention that the length of the thigh and lower leg bars is designed variably. Accordingly, the joint extensions according to FIGS. 4 and 5 can also be designed to be changeable with regard to their length. In addition, the bearing position of articulated axles $L_o$, $L_u$ and $M_u$, $M_o$ can be designed so that they are mounted in a changeable manner with respect to their height or lateral bearing position.

FIG. 6 shows the geometric relationships of an exoprosthesis according to the invention in a side view according to FIG. 2. The two joints 10, 11 are incorporated according to the invention so that their four-bar axles $L_o$, $L_u$ and $M_o$, $M_u$ run parallel to one another in two parallel planes and that lateral joint 10 is occupied [sic; displaced] with respect to medial joint 11 somewhat towards the posterior, that is, towards the back, by the measurement, $\Delta y$.

Such a joint formation represents a four-bar joint whereby the line marked F represents the thigh part and the line marked T forms the lower leg part. In the following examination, it is assumed that thigh part F stands firm and forms the stand. The relative movement of the lower leg with respect to the thigh is represented as movement of part T. Since the length of T is greater than the sum of the lengths of coupling links 13,14, articulated axle $L_o$ can move only towards the posterior, away from the initial position, which is marked bold. Articulated axle $M_u$ can move both towards anterior as well as towards posterior. In both cases, however, the distal extension of T, the lower leg, swings backwards. Both cases represent two possible bending movements of the knee, whereby each individual movement occurs automatically. In the anterior movement of articulated axle $M_u$, the latter moves further toward the anterior after exceeding the anterior dead-center position (coupling link 14 and line T form a straight line and coincide). The lower leg part can then assume the position $a_1$, indicated by thin lines. In the posterior movement of $M_u$, this articulated axle reaches its most posterior position in the posterior dead-center position (coupling link 13 and line T form a straight line and coincide, position $b_1$). As a consequence of further movement, $M_u$ then moves in the anterior direction. This movement occurs so slowly that in this further swinging of the lower leg part, articulated axle $M_u$ appears to remain at its location (position $b_2$ of T). In each case ($a_1$, $b_1$, $b_2$) the lower leg is swung backwards. The artificial joint is, thus, constructed so that under the effects of the forces actuated by pressure, the lower leg can only swing backwards.

Since medial joint 11 is displaced in the direction towards the thigh with regard to its articulated axles $M_u$ and $M_o$ by the measurement $\Delta x$, through the size of this displacement, the maximum pivoting angle μ max of the joint which corresponds to the maximum bending angle of the human knee can be influenced towards the posterior. In this way, the regularity is established that the greater the displacement $\Delta x$, the smaller the maximum pivoting angle μ max. Preferably, the displacement amount $\Delta x$ is selected such that the connection length F from $L_o$ to $M_u$ describes an angle a with respect to the horizontal line which is between 0° and 45°: 0°<a<45°. It is also within the scope of the present invention that lateral joint 10 and medial joint 11 are arranged so that the planes through their coupling links 13,14 run spatially inclined towards one another from which results a spherical course of movement.

We claim:

1. An exoprosthesis for the human knee joint comprising:
   a thigh part (1) and a lower leg part (6);
   the lower leg part (6) and the thigh part (1) being mutually interconnected by a four-joint arrangement including a medial joint (11) and a lateral joint (10);
   the medial joint and the lateral joint respectively having a joint geometry of a joint chain with coupling elements (13, 14) and two joint axles ($M_u$, $M_o$; $L_u$, $L_o$), wherein the joint geometry of the medial joint (11) forms a folded dimeric chain and the joint geometry of the lateral joint (10) forms an extended dimeric joint chain, where the joint axles ($L_o$, $L_u$) of the lateral joint (10) are coupled in an articulated fashion by the coupling element (13) and the joint axles ($M_u$, $M_o$) of the medial joint are coupled in an articulated fashion by the coupling element (14);
   the joint axle ($M_u$) between the lower part (6) and the coupling element (14) of the medial joint (11) being offset relative to the joint axle ($M_o$), between the coupling element (14) and the thigh part (1), in a direction toward the thigh part (1) in an extended position of the knee joint;
   the joint axle ($L_u$) between the lower leg part (6) and the coupling element (13) of the lateral joint (10) being connected in an articulated fashion to the thigh part (1) at the joint axle ($L_o$) and being offset, relative to the joint axle ($L_o$), in a direction toward the lower leg part (6);

whereby in the extended position of the knee joint, the coupling elements (13, 14) extend parallel in two parallel planes that respectively intersect with the joint axles of the lateral joint ($L_o$, $L_u$) and the medial joint ($M_u$, $M_o$);

the lateral joint (10) is offset relative to the medial joint (11) in the posterior direction by a distance ($\Delta y$) that corresponds to the distance between the two parallel planes; and the joint axles ($M_u$, $M_o$) of the medial joint (11) are offset relative to the lateral joint (10) in the direction toward the thigh (3) by a distance ($\Delta x$) that corresponds to the distance between the joint axles ($L_o$, $M_o$.

2. The exoprosthesis according to claim 1, wherein:

the thigh part (1) comprises two thigh braces (2,2a) that extend on the inner and outer side of the thigh (3) of a human leg (4) and are connected to one another by lateral braces (5) that encompass the thigh (3);

the lower leg part (6) comprises two lower leg braces (7,7a) that are arranged on the medial and the lateral side of the lower leg (8) of a human leg (4); and the lower leg braces (7,7a) are connected to one another by lateral braces (9) that encompass the lower leg (8).

3. The exoprosthesis according to claim 2, wherein:

the lateral joint (10) and the medial joint (11) are collectively arranged on the lateral side of the human knee;

the medial joint (11) is formed by an extension (16) of the lower leg brace (7) that overlaps a bearing end of the thigh brace (2) in the direction toward the thigh and, viewed laterally in the direction toward the human knee, ends behind the bearing end of the thigh braces (2) such that the lateral joint (10) and the medial joint (11) by the distance ($\Delta y$); is parallel to the coupling element (14) of the medial joint (11), viewed in the direction toward the knee, is coupled to the bearing end of the thigh brace behind said thigh brace by means of the joint axle $M_u$.

4. The exoprosthesis according to claim 1, wherein:

the lateral joint (10) and the medial joint (11) are respectively fastened to a thigh stub (20) and a lower leg stub (21) that forms part of a lower leg prosthesis;

the lateral joint (10) is formed by a bearing extension (22) of the thigh stub (20) and a bearing extension (23) of the lower leg stub (21);

both bearing extensions are connected to one another in articulated fashion by a coupling element (13,14);

the medial joint (11) is formed by a joint extension (25) on the thigh stub (20) and a joint extension (26) on the lower leg stub (21);

the joint extension (26) overlaps the joint extension (25) and lies between the joint extension (25) and the bearing extension (22); and the coupling element (14) is arranged between the two joint extensions (25,26).

* * * * *